United States Patent [19]

Abraham et al.

[11] Patent Number: 4,537,064
[45] Date of Patent: Aug. 27, 1985

[54] METHOD AND APPARATUS FOR MEASURING SHEAR MODULUS AND VISCOSITY OF A MONOMOLECULAR FILM

[75] Inventors: Bernard M. Abraham, Oak Park, Ill.; Kenjiro Miyano, Sendai, Japan; John B. Ketterson, Evanston, Ill.

[73] Assignee: The United States of America as represented by the United States Department of Energy, Washington, D.C.

[21] Appl. No.: 542,957

[22] Filed: Oct. 18, 1983

[51] Int. Cl.³ .................... G01N 11/16; G01N 13/02
[52] U.S. Cl. .......................................... 73/54; 73/64.4
[58] Field of Search ................. 73/53, 54, 59, 60, 64.4

[56] References Cited

U.S. PATENT DOCUMENTS 4,413,506 11/1983 Abraham et al. .................... 73/64.4

OTHER PUBLICATIONS

Abraham et al., *A Wide Range High Sensitivity Film Balance*, in Rev. Sci. Instr., vol. 51(8), pp. 1083–1087, Aug. 1980.
Sohl et al., *Novel Technique for Dynamic Surface Tension and Viscosity Measurements at Liquid–Gas Interfaces*, in Rev. Sci. Instr., vol. 49(10), pp. 1464–1469, Oct. 1978.
Abraham et al., *Centro-Symmetric Technique for Measuring Shear Modulus, Viscosity & Surface Tension of Spread Monolayers*, in Rev. Sci. Instr., vol. 52(2), pp. 213–219, Feb. 1983.
Fromherz, *Instrum. for Handling Monomolecular Films at Air–Water Interface*, in Rev. Sci. Instr., vol. 46(10), pp. 1380–1385, Oct. 1975.

*Primary Examiner*—Stewart J. Levy
*Assistant Examiner*—Joseph W. Roskos
*Attorney, Agent, or Firm*—Jeannette M. Walder; Walter L. Rees; Judson R. Hightower

[57] ABSTRACT

Instrument for measuring the shear modulus of a monomolecular film comprises a circular trough having inwardly sloping sides containing a liquid for supporting the monolayer on the surface thereof; a circular rotor suspended above the trough such that the lower surface of the rotor contacts the surface of the liquid, positioned such that the axis of the rotor is concentric with the axis of the trough and freely rotable about its axis; apparatus for hydrostatically compressing the monolayer in the annular region formed between the rotor and the sides of the trough; and apparatus for rotating the trough about its axis. Preferably, hydrostatic compression of the monolayer is achieved by removing liquid from the bottom of the trough (decreasing the surface area) while raising the trough vertically along its axis to maintain the monolayer at a constant elevation (and maintain rotor contact). In order to measure viscosity, a apparatus for rotating the rotor about its axis is added to the apparatus.

15 Claims, 8 Drawing Figures

METHOD AND APPARATUS FOR MEASURING SHEAR MODULUS AND VISCOSITY OF A MONOMOLECULAR FILM

CONTRACTUAL ORIGIN OF THE INVENTION

The U.S. Government has rights in this invention pursuant to Contract No. W-31-109-ENG-38 between the U.S. Department of Energy and the University of Chicago representing Argonne National Laboratory.

BACKGROUND OF THE INVENTION

This invention relates generally to a method and apparatus for measuring mechanical properties of a monomolecular film, and, more particularly to a method and apparatus for measuring shear modulus and viscosity of a monomolecular film (monolayer).

The principle property studied of monolayers has been the surface pressure, $\pi$, as a function of the molecular area density. Surface pressure is defined as the difference between the surface tension of pure water and that of the monolayer covered water and is usually displayed as a function of the area per molecule, i.e. the $\pi$-A diagram. The $\pi$-A diagram has many characteristics of a P-V diagram in three dimensions and the observed features have, by analogy, been assigned phase labels similar to those in three dimensions.

In addition to the $\pi$-A diagram, measurements of surface potential and surface viscosity have been made for some monolayers. Surface viscosity has been measured by rotational or channel viscometers. Rotational viscometers used in the past lacked sensitivity and acted as an obstruction to material flow during compression. Channel viscometers are unreliable because the pressure is not hydrostatic for films that can support a shear. Prior to the present invention, no techniques have been available that are capable of determining shear modulus. Shear modulus is an important parameter in that it distinguishes a liquid from a solid: only a solid can support a shear.

Many substances have $\pi$-A diagrams with a kink which has been interpreted to mean a phase change from liquid to solid. Correlation of shear modulus measurements with the $\pi$-A diagrams will provide useful information on the properties of monolayers.

Therefore, it is an object of the present invention to provide a method and apparatus for measuring shear modulus of a monomolecular film.

It is also an object of the present invention to provide an improved method and apparatus for measuring viscosity of a monomolecular film.

Additional objects, advantages, and novel features of the invention will be set forth in part in the description which follows, and in part will become apparent to those skilled in the art upon examination of the following or may be learned by practice of the invention.

SUMMARY OF THE INVENTION

To achieve the foregoing and other objects and in accordance with the purposes of the present invention, apparatus for measuring the shear modulus of a monomolecular film (monolayer) may comprise a circular trough having inwardly sloping sides containing a liquid for supporting the monolayer on the surface thereof; a circular rotor suspended above the trough such that the lower surface of the rotor contacts the surface of the liquid, positioned such that the axis of the rotor is concentric with the axis of the trough and freely rotable about its axis; means for hydrostatically compressing the monolayer in the annular region formed between the rotor and the sides of the trough; and means for rotating the trough about its axis. Preferably, hydrostatic compression of the monolayer is achieved by removing liquid from the bottom of the trough (decreasing the surface area) while raising the trough vertically along its axis to maintain the monolayer at a constant elevation (and maintain rotor contact). In order to measure viscosity, a means for rotating the rotor about its axis is added to the apparatus.

A unique aspect of the invention is the ability to hydrostatically compress the monolayer without any obstructions in the path of the compression and is achieved as follows. The monolayer is placed on the surface of a liquid contained in an inverted conical trough. As a consequence of the sloping sides, the diameter of the liquid surface is a function of the distance from the top. The area of the liquid surface as a function of the distance, Z, from the top of the trough is:

$$A = \pi/4[D - 2Z \tan \theta]^2 \qquad (1)$$

where D is the diameter of the top of the trough and $\theta$ is the inclination of the sides from vertical. The free area available to the monolayer is the area in the annular region between the rotor and trough walls: the value calculated from equation (1) minus the area of the rotor in contact with the liquid surface. The rotor must have a circular cross-section and be positioned concentric with the axis of the trough to eliminate obstruction of the monolayer. Lowering the liquid level in the trough, such as by draining it from the bottom, isotropically compresses the film. As the liquid is withdrawn from the trough, the trough is raised to maintain the surface at a constant level. This insures contact between the rotor and the liquid surface and is also important when the present invention is used in conjunction with a capillary wave system, which enables determination of the absolute surface tension from which $\pi$ is derived. A compatible capillary wave system is described at Sohl et al., Rev. Sci. Instrum. 49, 1464 (1978).

A method of measuring the shear modulus of a monomolecular film (monolayer) may comprise: forming a monolayer on the surface of a liquid contained in a circular trough having inwardly sloping sides; suspending a circular rotor above the trough such that the lower surface of the rotor contacts the surface of the liquid and positioned such that the axis of the rotor is concentric with the axis of the trough; hydrostatically compressing the monolayer in the annular region formed between the rotor and the sides of the trough; rotating the trough about its axis through an angle $\beta$, where $\beta \neq 0$; and detecting the motion of the rotor in response to the trough's rotation. When the trough is rotated through an angle $\beta$ and then held in this position, the rotor will rotate through an angle $\alpha$ to a new equilibrium position if the shear modulus is not zero. Dynamic viscosity may be measured by applying a moment to the rotor about its axis and detecting the resultant damping of the oscillations of the rotor in response to the applied moment.

DETAILED DESCRIPTION OF THE INVENTION

Figure 1:
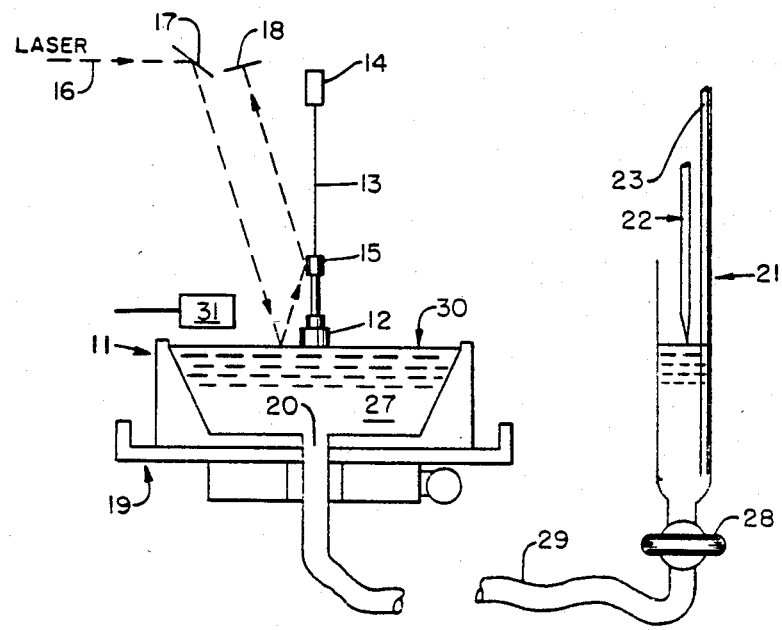
FIG. 1 is a schematic of the apparatus for measuring shear modulus and viscosity of a monomolecular film.

Referring to FIG. 1, trough 11 is machined from a teflon pancake to have a circular cross-section and sloping inner sides and holds water 27. Trough 11 is connected to rotatable table 19 which is capable of precise rotation about its axis with a motor driven flexible shaft (not shown) as well as vertical movement along its axis. The angular position of trough 11 is determined with a linear variable differential transformer (not shown) to $5 \times 10^{-3}$ degrees. Table 19 can be raised continuously by a stainless steel cable to a motor drive (not shown) with a positioning accuracy of 0.05 mm. Drain 20 at the bottom of trough 11 is connected by flexible tubing 29 to buret 21. Stainless steel capillary 23 projects into buret 21 and extends to stop-cock 28. Level sensor electrode 22 projects part way into buret 21.

Rotor 12, also fabricated of teflon, is suspended by torsion wire 13 (either a stainless steel or platinum alloy wire), and located accurately in the center of trough 11. Stainless steel mirror 15 is connected to rotor 12 and rotates with rotor 12. Both rotor 12 and mirror 15 can be rotated by stepping motor 14 programmed in increments of 0.27°. Alternatively the rotor and mirror can also be rotated by suspending from a two turn coil in a magnetic field.

Figure 5:
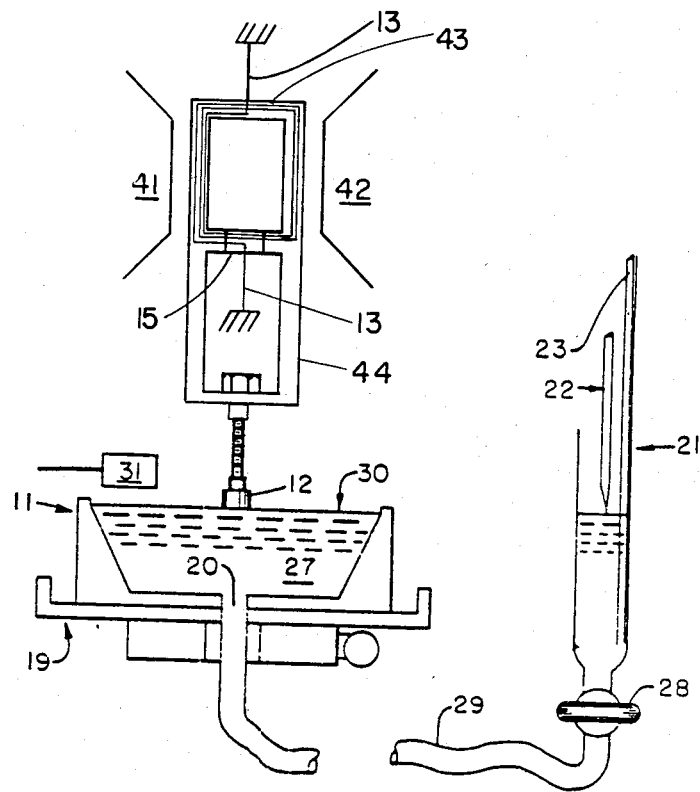
FIG. 5 is a schematic of the apparatus for measuring shear modulus and viscosity of a monomolecular film showing an alternate means for rotating the rotor and mirror.

Referring to FIG. 5 torsion wire 13 is connected to two turn coil 43. Rotor 12 is mounted to frame 44 which supports coil 43 and mirror 15. Coil 43 is placed between magnets 41 and 42 which provide the magnetic field. Movement of rotor 12 causes the current through coil 43 to vary which is indicative of shear modulus.

A separate capillary wave system is used to determine the absolute surface tension of pure water and that of the monolayer covered water. Waves are excited through electro-capillarity which requires a potential difference between the water 27 and the wave generator. The potential difference is established between wave generator electrode 31, which generates waves and is located just above the water surface, and level sensor electrode 22 which just contacts the water in buret 21. The water is acidified and thus provides a conducting path between electrode 31 and sensor 22 through stop-cock 28 and flexible tube 29.

Film 30, which is placed on the surface of water 27, is uniformly compressed in the following manner. Stop-cock 28 is closed and an aliquot of water is withdrawn from buret 21 through capillary 23. Stop-cock 28 is then partially opened and water flows slowly from trough 11 to buret 21 compressing film 30 by reducing the surface area. Since the water level in buret 21 has been lowered breaking contact with electrode 22, there is no capillary wave. When the water level in trough 11 equals that in buret 21, stop-cock 28 is fully opened and trough 11 is slowly raised. This causes more water to flow out of trough 11 into buret 21 compressing film 30 further and raises the water level in buret 21. When the overall water level in buret 21 reaches electrode 22, the capillary wave reappears and trough 11 is stopped.

A single laser beam 16 is used as the sensor for all measurements. The beam is directed onto the film surface by mirror 17. A fraction of the beam is reflected by film 30 onto stainless steel mirror 15, which is then reflected onto position sensing photodiode 18.

Figure 3:
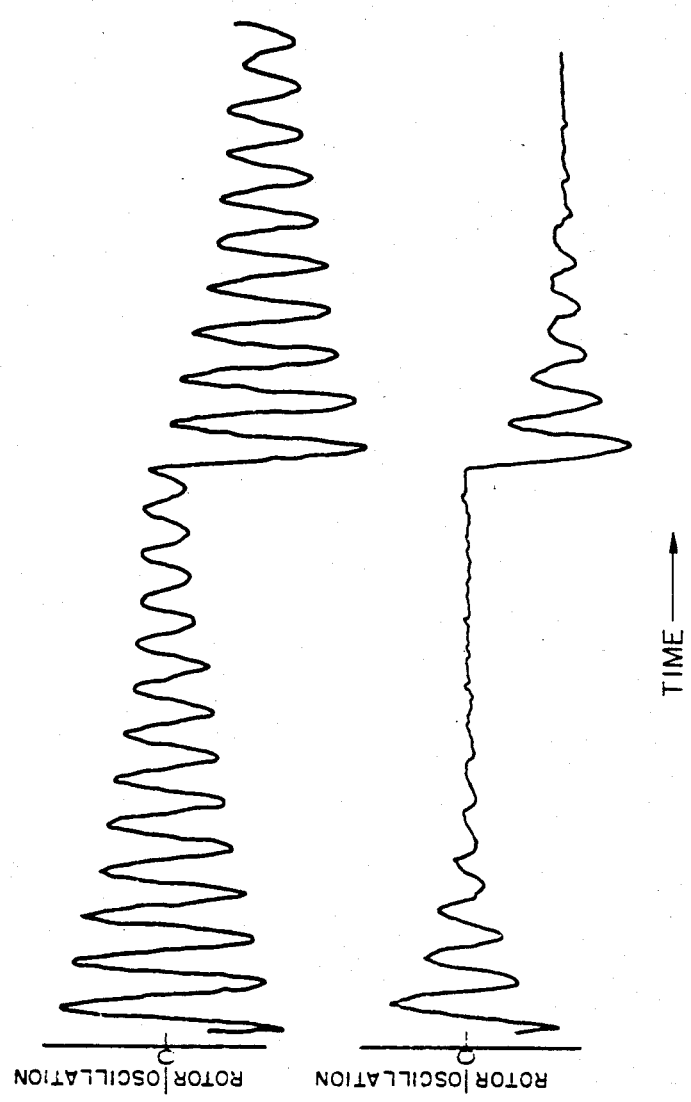
FIGS. 3A–B are graphs of rotor oscillation on water without a film (3A) and with a film at low density (3B).

The dynamic viscosity of water and film covered water is determined from the damping of the oscillations of rotor 12. Stepping motor 14 is pulsed, which displaces rotor 12 by 0.27°. The damped oscillatory light signal is collected by the photodiode receiver (not shown) and stored in the memory of the signal averager (not shown). When the oscillations have receded into noise, the rotor is stepped in the opposite direction and these signals are collected in the second half of the memory to complete one sweep. Usually eight sweeps are accumulated to complete one point. The damped sine wave as then fitted by an online computer to obtain damping coefficient, base line, and frequency. FIG. 3A shows oscillation damping of the rotor in water without a film and FIG. 3B with a film at low density.

Figure 4:
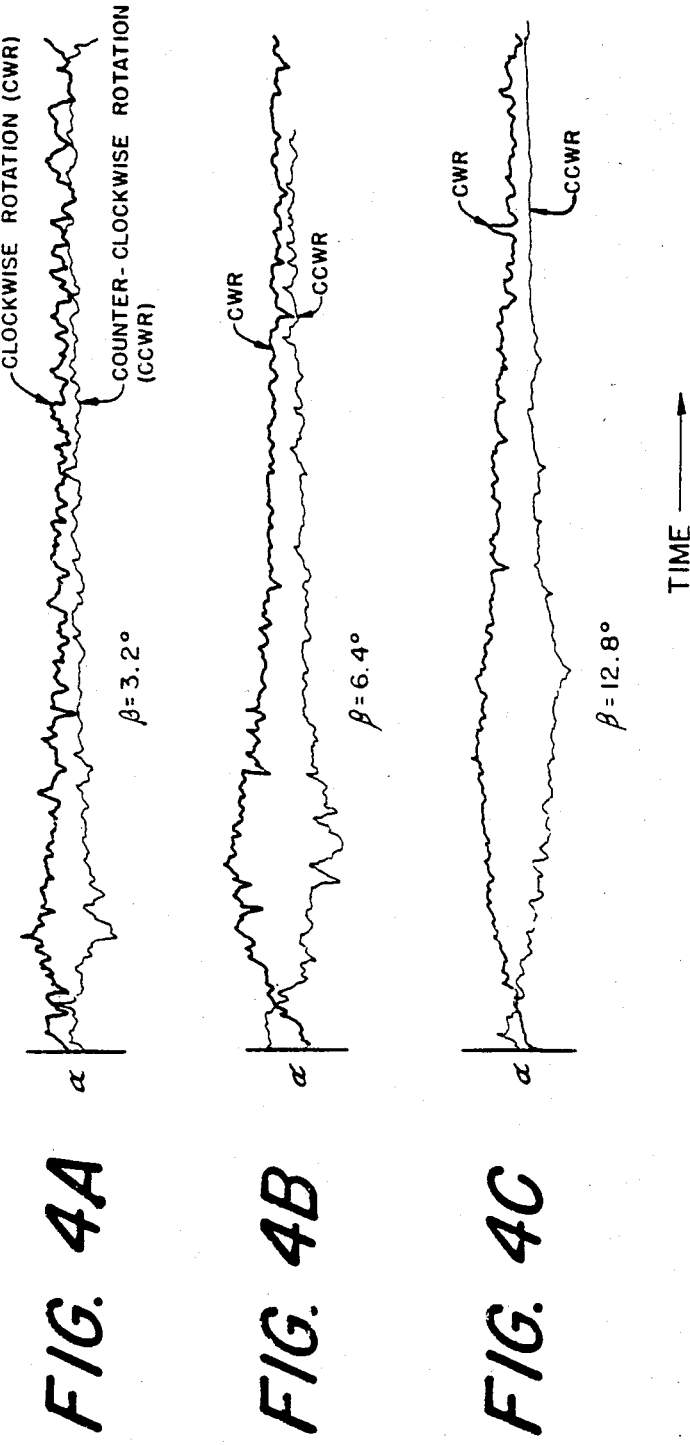
FIGS. 4A–C are graphs of rotor angular displacement at various amounts of trough rotation, $\beta$.

To perform the static shear measurement, the signal averager was triggered as table 19 commenced rotation. Data from the photodiode was collected for a period of time before table rotation was reversed. A clockwise and counterclockwise rotation comprised one sweep. Usually four sweeps were taken. FIGS. 4A–4C show angular displacement, $\pi$, of the rotor with various trough rotations, $\beta$.

EXAMPLE

Figure 2:
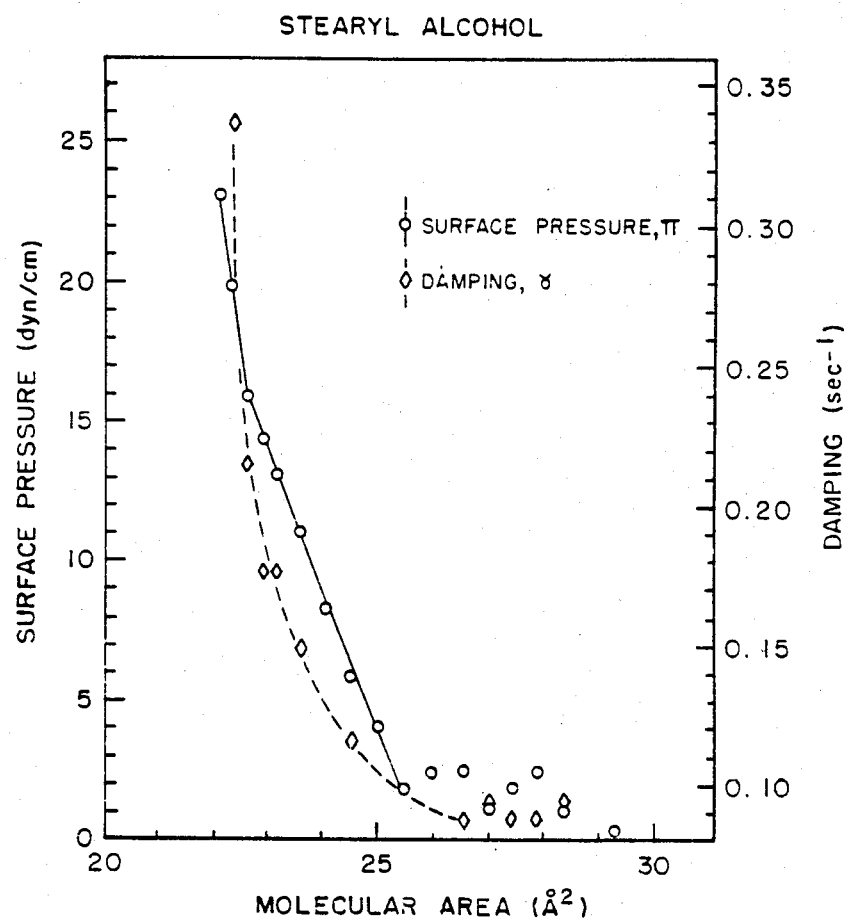
FIG. 2 is a graph of surface pressure, $\pi$, and rotor damping time constant, $\tau$, vs. molecular area, A, for a stearly alcohol film spread on pH3 water at 24° C.

The $\pi$-A diagram and damping coefficient for stearyl alcohol were obtained using the invention and are plotted in FIG. 2. The area per molecule seems to be slightly larger than published data, but the so-called liquid-solid phase change (kink in graph) is clearly seen. The scatter at low values of $\pi$ is due to inhomogeneity in the film which is typical in the so-called condensed liquid phase at a large area. Dynamic viscosities of $2 \times 10^{-3}$ surface poise at $\pi \sim 2$ dyne/cm and $2 \times 10^{-2}$ surface poise at $\pi \sim 20$ dyne/cm were calculated from these measurements. These values are about one order of magnitude smaller than previous published data. This discrepancy is partly due to the prior complete neglect of the effect of the underlying water. Static shear modulus of $1 \times 10^{-3}$ dyne/cm at $\pi = 20$ dyne/cm was also obtained.

The embodiments of this invention in which an exclusive property or privilege is claimed are defined as follows:

1. Apparatus for measuring the shear modulus of a monomolecular film (monolayer) comprising:
   (a) a circular trough having inwardly sloping sides, containing a liquid for supporting said monolayer on the surface thereof;
   (b) a circular rotor suspended above the trough such that the lower surface of the rotor contacts the surface of the liquid, positioned such that the axis of the rotor is concentric with the axis of the trough, and freely rotable about its axis;
   (c) means for hydrostatically compressing said monolayer in the annular region formed between the rotor and the sides of the trough; and
   (d) means for rotating the trough about its axis.

2. The apparatus of claim 1 further comprising means for detecting rotation of the rotor.

3. The apparatus of claim 1 wherein said hydrostatic compressing means comprises:
  means for removing liquid from the trough, while maintaining rotor contact with the liquid surface.

4. The apparatus of claim 1 wherein said liquid is water.

5. The apparatus of claim 1 wherein said trough is lined with teflon.

6. The apparatus of claim 2 wherein said detection means comprises a stainless steel mirror connected to the rotor and rotable with the rotor, means for generating a beam of light directed towards the monolayer; and a photodiode for sensing the light reflected from the monolayer surface to said mirror surface.

7. The apparatus of claim 2 further comprising a capillary wave system for measuring surface tension of said liquid and of said monolayer covered liquid.

8. Apparatus for measuring the viscosity of a monolayer comprising:
  (a) a circular trough having inwardly sloping sides, containing a liquid for supporting said monolayer on the surface thereof;
  (b) a circular rotor suspended above the trough such that the lower surface of the rotor contacts the surface of the liquid, positioned such that the axis of the rotor is concentric with the axis of the trough, and freely rotable about its axis;
  (c) means for hydrostatically compressing said monolayer in the annular region formed between the rotor and the sides of the trough; and
  (d) means for rotating the rotor about its axis.

9. The apparatus of claim 8 further comprising means for detecting rotation of the rotor.

10. The apparatus of claim 8 wherein said rotor rotation means comprises a torsion wire connecting said rotor to a stepping motor.

11. The apparatus of claim 8 wherein said rotation means comprises a two turn coil in a magnetic field.

12. A method for measuring the shear modulus of a monomolecular film (monolayer) comprising the steps of:
  (a) forming a monolayer on the surface of a liquid contained in a circular trough having inwardly sloping sides;
  (b) suspending a freely rotable circular rotor above the trough such that the lower surface of the rotor contacts the surface of the liquid and positioned such that the axis of the rotor is concentric with the axis of the trough;
  (c) hydrostatically compressing said monolayer in the annular region formed between the rotor and the sides of the trough;
  (d) rotating the trough about its axis through an angle $\beta$, where $\beta \neq 0$; and
  (e) detecting the motion of the rotor in response to the trough's rotation.

13. The method of claim 12 wherein said monolayer is hydrostatically compressed by:
  removing liquid from the trough so that the surface area of said annular region is reduced, while maintaining rotor contact with the liquid surface.

14. A method of measuring the viscosity of a monolayer comprising the steps of:
  (a) forming a monolayer on the surface of a liquid contained in a circular trough having inwardly sloping sides;
  (b) suspending a freely rotable circular rotor above the trough so that the lower surface of the rotor contacts the surface of the liquid and positioned such that the axis of the rotor is concentric with the axis of the trough;
  (c) hydrostatically compressing said monolayer in the annular region formed between the rotor and the sides of the trough;
  (d) applying a moment to the rotor about its axis; and
  (e) detecting the damping of the free oscillations of the rotor in response to said moment.

15. The method of claim 14 wherein said monolayer is hydrostatically compressed by:
  removing liquid from the trough so that the surface area of said annular region is reduced, while maintaining contact with the liquid surface.

* * * * *